United States Patent [19]

Becker et al.

[11] 4,276,057
[45] Jun. 30, 1981

[54] PROCESS FOR TREATING PRESSURIZED GASES TO REMOVE UNWANTED COMPONENTS

[75] Inventors: Hans Becker, Munich; Peter Grimm, Pullach; Gerhard Ranke, Pöcking; Dieter Roth, Unterhaching, all of Fed. Rep. of Germany

[73] Assignee: Linde Aktiengesellschaft, Hollriegelskreuth, Fed. Rep. of Germany

[21] Appl. No.: 51,359

[22] Filed: Jun. 25, 1979

[30] Foreign Application Priority Data

Jun. 29, 1978 [DE] Fed. Rep. of Germany ....... 2848498

[51] Int. Cl.³ .............................................. B01D 19/00
[52] U.S. Cl. ........................................ 55/40; 55/48; 55/49; 55/73
[58] Field of Search ................... 55/48, 49, 57, 68, 73, 55/88, 40

[56] References Cited

U.S. PATENT DOCUMENTS

| | | | |
|---|---|---|---|
| 2,026,265 | 12/1935 | Bennett | 55/48 |
| 2,596,785 | 5/1952 | Nelly, Jr. et al. | 55/73 |
| 2,815,650 | 12/1957 | McIntire | 55/48 |
| 2,849,371 | 8/1958 | Gilmore | 55/88 |
| 3,130,026 | 4/1964 | Becker | 55/68 |
| 3,213,154 | 10/1965 | Bauer | 55/73 |
| 4,012,212 | 3/1977 | Kniel | 55/68 |

*Primary Examiner*—Bernard Nozick

[57] ABSTRACT

Process for treating a gaseous mixture under pressure to remove unwanted components from a gas, including methane, ethane, hydrogen, nitrogen, such components as $C_3$, $C_4$ and $C_5$ higher hydrocarbons, hydrogen sulphide and carbon dioxide. The gaseous mixture is fractionated under pressure to remove in bottoms product portions of higher hydrocarbons, hydrogen sulphide and carbon dioxide. The overhead product is scrubbed to remove in a suitable solvent a substantial portion of or all of the remaining higher hydrocarbons, hydrogen sulphide and carbon dioxide.

13 Claims, 1 Drawing Figure

PROCESS FOR TREATING PRESSURIZED GASES TO REMOVE UNWANTED COMPONENTS

FIELD OF THE INVENTION

This invention relates to process and apparatus for treating a gaseous mixture which includes methane, ethane, hydrogen and nitrogen wherein unwanted components, such as higher hydrocarbons, hydrogen sulphide and carbon dioxide are removed.

BACKGROUND OF THE INVENTION

In mixtures of gas, such as natural gas, gas accompanying petroleum, cracked gas, synthesis gas, coke-oven gas, coal-gasification and distillation gas, it is in many cases necessary and desirable, to remove therefrom acid gases, such as carbon dioxide and hydrogen sulphide, and to separate specific hydrocarbon fractions. The removal of the acid gases is necessary because, as a rule, they interfere with the further processing thereof for a wide range of industrial purposes. Carbon dioxide is at least a ballast substance which requires inefficient enlargement of the equipment and which must frequently be removed because of subsequent processing requirements. Hydrogen sulphide is a noxious substance which cannot simply be released into the atmosphere and which, if it is used for burning may lead to inadmissible concentrations of sulphur dioxide in the exhaust gases. The purpose of removing various hydrocarbon fractions, especially if natural gas is to be used for burning, is to recover the considerable concentration of higher hydrocarbons frequently present in such gases. They may be used for engine propellants or as the starting materials for chemical syntheses of other petro-chemical products.

German Pat. No. 971.786 discloses a variety of methods of conditioning mixtures of gas containing not only hydrocarbons, but also carbon dioxide and hydrogen sulphide. It is suggested that sulphur compounds, $C_3$-to $C_5$-hydrocarbons, carbon dioxide, water vapour and resin-formers can be scrubbed in one operation from natural gases with the aid of inorganic, neutral, polar solvents, at temperatures as low as $-150°$ C. It is furthermore proposed to scrub out polar contaminants, at about $-40°$ C., with methanol as a solvent and then to dissolve out the $C_3$- to $C_4$-hydrocarbons with a mixture of $C_5$-to $C_7$-hydrocarbons. It has been found, however, that the polar scrubbing agent also dissolved undesirably large amounts of $C_3$- and $C_4$-hydrocarbons and, as a remedy for this, water was added to the methanol.

If it is particularly important to wash out $C_3$ or higher hydrocarbons, German Pat. No. 971.786 suggests a further modification of the method, whereby the hydrocarbons are first separated with the aid of a neutral unpolar solvent to which is added a small amount of a neutral polar solvent. After this, the polar contaminants are removed from the gas, especially hydrogen sulphide and carbon dioxide, in a subsequent scrubbing stage, at a low temperature, with a lower alcohol. Water may be added to the lower alcohol to reduce the solubility of methane and ethane in the solvent. Further, it is proposed, in German Pat. No. 971,786, to cool the gas containing the hydrocarbons until pentane and the higher hydrocarbons condense out and then to scrub the $C_3$- and $C_4$-hydrocarbons, together with the $H_2S$ and $CO_2$, out of the gas with a neutral polar solvent.

However, all of these known methods have the disadvantage that the polar compounds, carbon dioxide and hydrogen sulphide, are always removed exclusively by scrubbing operations with considerable quantities of solvent, in part even together with considerable amounts of hydrocarbons. This is extremely disadvantageous, particularly in view of the thermal loading and the cost of regenerating the solvent.

It is, therefore, an object of the present invention to provide a method and an apparatus for conditioning or treating mixtures of gas containing hydrocarbons, hydrogen sulphide, and carbon dioxide, which will overcome several of the disadvantages of known methods.

SUMMARY OF THE INVENTION

The invention optimizes on the energy requirements of the system for purposes of conditioning the gaseous mixture. The principal portion of the separation is effected in a rectification stage prior to scrubbing. As a result, the scrubbing stage is relied on as a secondary step in the removal of impurities or unwanted components. The extent of separation of the gaseous mixture in the rectification stage is dependent upon the composition of the gas and the pressure of the gas during fractionation. However, the rectification stage is designed such that it separates from the gaseous mixture a portion of the unwanted components, including the higher hydrocarbons, to substantially reduce the demand during the scrubbing stage in removing the remainder of the unwanted components, thereby substantially reducing the costs of regenerating the scrubbing solvent.

The process, according to this invention, for treating a gaseous mixture under pressure, which includes methane, ethane, hydrogen, nitrogen and unwanted components, such as $C_3$, $C_4$ and $C_5$ higher hydrocarbons, hydrogen sulphide and carbon dioxide, comprises fractionating under pressure such gaseous mixture to remove in bottoms product portions of higher hydrocarbons, hydrogen sulphide and carbon dioxide. The overhead product of the fractionation is scrubbed to remove in a suitable solvent a substantial remainder of higher hydrocarbons, hydrogen sulphide and carbon dioxide.

The apparatus, according to the invention, for treating such gaseous mixture comprises a fractionation column into which such pressurized gases are delivered. The fractionation column is adopted to provide a column bottoms product portions of higher hydrocarbons, hydrogen sulphide and carbon dioxide. Means is provided for removing such column bottoms product from the fractionation column and transfer it for subsequent processing to recover any remaining desired components therein. Means is provided for transferring column overhead product to a scrubbing device, wherein the overhead product is contacted with a suitable solvent to remove a substantial remainder of higher hydrocarbons, hydrogen sulphide and carbon dioxide.

BRIEF DESCRIPTION OF THE DRAWINGS

Preferred embodiments of the invention are shown in the drawings wherein.

DETAILED DESCRIPTION OF THE PREFERRED EMBODIMENTS OF THE INVENTION

Figure 1:
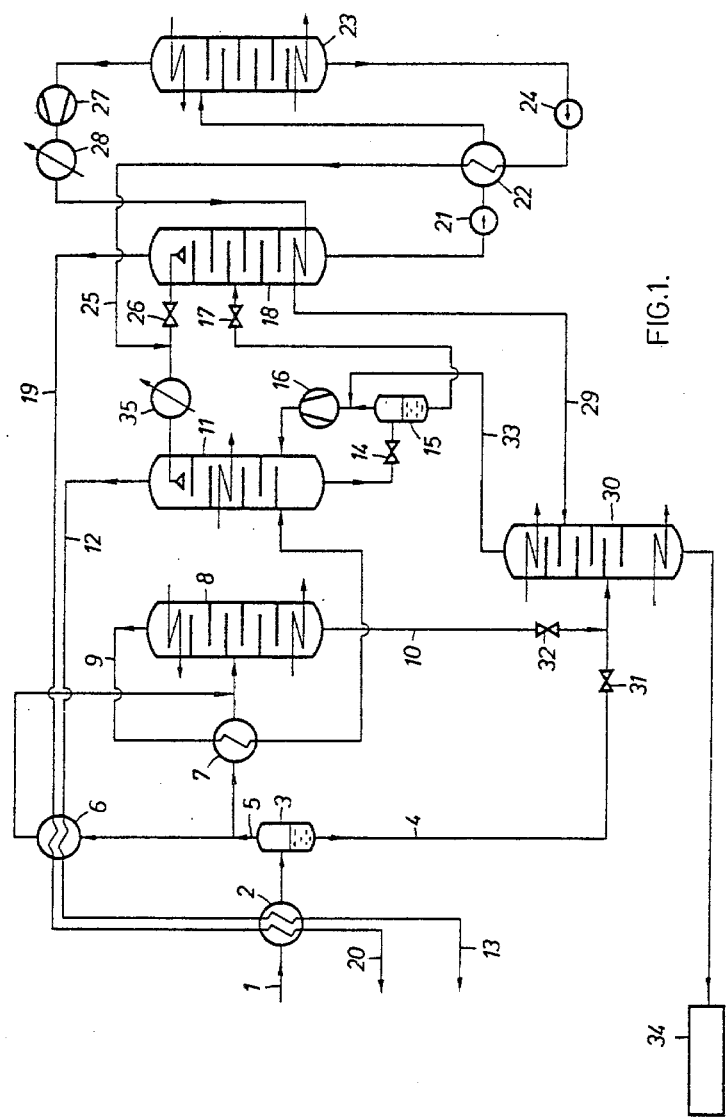
FIG. 1 is a schematic flow chart of the process wherein components of the apparatus are represented.

Design criteria to be considered with respect to the system shown in FIG. 1 are, as mentioned, dependent upon the properties and state of the gaseous mixture to be treated. The invention is based on the preception that it is necessary for a thermodynamically optimum processing to transfer the better portion of the separation business into the rectification before the washing step and to leave to the washing step only that portion which can not be managed in the rectification for physical reasons, e.g. precipitation of solids or formation of an azeotropic mixture. The minimum demand the rectification has to fulfill is the complete separation of those components which form mixtures with the washing agent which are only difficultly separable and would therefore require great expenditure in the regeneration of the washing agent. The optimum distribution of the separation work between the rectification and the washing step is largely dependent on the composition of the gases and the processing pressure. During the rectification stage of the process, the operating pressure in the fractionation column should be less than the minimum critical pressure of the liquid mixtures formed during the rectification. According to an aspect of this process, the rectification may be carried out in a range of pressures between the critical pressure of the individual hydrocarbons in the mixture and the minimum critical pressure of the formed liquid phases. It is appreciated, however, that the process may be carried out at pressures below the critical pressures of the individual hydrocrbons.

Definite advantages are realized in operating the fractionation column in the range between the critical pressures of the individual components and the lowest critical pressure of the liquid mixtures. For example, in conditioning natural gas, it is usually necessary to relese the treated gas under high pressure in order to keep the desired properties for pipeline transport. Also, the natural gas is usually received is at high pressure. Thus, the treating process should be conducted at these higher pressure ranges to reduce the need for major pressure-relieving devices during processing and/or compressors to return the treated gas to the higher transport pressures. A further advantage realized in operating at the higher pressures is that the temperature during fractionation may be higher than if the constituents were at lower pressure, so that the cost of refrigeration during processing is substantially lowered. In any case in the inventive process the selectivity and the cut in the rectification column have to be chosen so that the critical pressure of the liquid phase on each tray of the rectification column surmounts the column pressure. In consequence the optimum cut in the rectification column can vary in a wide range depending on the composition of the raw gas and the processing pressure.

In selecting the cut, consideration should also be given to the gaseous composition. For example, in treating a gas containing relatively little carbon dioxide and hydrogen sulphide, but rich in the heavy hydrocarbons, it would be preferable to carry out the rectification in a manner that the overhead gas of the fractionation column is completely free of the $C_5$ and heavier hydrocarbons, but that with the bottoms product also $C_1$ and $C_2$ hydrocarbons are removed. This type of rectification eliminates the need during the subsequent scrubbing stage for the methanol or other selected solvents to remove the $C_5$ hydrocarbons. This avoids a significant problem particularly with a solvent like methanol, because the $C_5$ hydrocarbons form an azeotropic mixture with methanol, thereby adding substantially to the regeneration cost of the solvent for subsequent scrubbing stages.

In another instance, should the gaseous mixture contain relatively large amounts of carbon dioxide and hydrogen sulphide it may be preferable to conduct the rectification in a manner that the $C_4$ and heavier hydrocarbons and most of the $C_3$ hydrocarbons and hydrogen sulphide are collected in the column bottoms, whereas the carbon dioxide, $C_1$ and $C_2$ hydrocarbons are removed with the overhead product.

The aspect of fractionating the gaseous mixture prior to scrubbing results in a considerable reduction in power consumption in the scrubbing operation, in terms of removal of the heat of absorption and for regeneration of the scrubbing solvent. In general the gas to be fractionated is first cooled prior to fractionation to condense higher hydrocarbons, which are treated separately, whereafter the gaseous phase is further cooled and the resulting liquid-gas-mixture fed into the rectification column.

However, it is likewise possible to install a second separation step between the first one and the fractionation and to subject only the liquid to fractionation, while the gaseous phase is commingled with the fractionation overhead.

The choice of the suitable variant depends on the gas to be treated. In the second variant the fractionation column may become smaller due to a reduced throughput. This fact and a rising dew point of the overhead result in a reduced cold requirement in the head of the fractionation. On the other side of the second condensation the temperature has to be lowered in the second variant, because it is necessary to condense more components in order to get a tailgas clean enough for the scrubbing step.

The overhead product of the fractionation column together with tailgas from the second separation, if any, passes into a scrubbing column where it is scrubbed with any suitable solvent. Examples of the solvents may be polar organic solvents such as dimethyl formamide or N-methyl pyrrolidone. A preferred solvent is methanol. Such solvents are particularly useful in contacting and removing from the mixture the unwanted carbon dioxide, hydrogen sulphide and any residues of heavy hydrocarbons.

In view of desirability of maintaining high operating pressures, the scrubbing operation should be carried out under pressure and preferably at low temperatures usually below 0° C., in order to increase the solubility of the unwanted components in the scrubbing solvent. Due to the rectification stages being carried out at the higher pressure, there is, therefore, no need to compress the overhead product prior to entering the scrubbing column to again conserve on energy requirements for the overall system.

The scrubbing of the overhead products from the fractionation column may be accomplished in two stages, the first stage being operated with partially regenerated solvent and the second one with strongly regenerated solvent. This approach reduces the cost of the solvent regeneration as compared with other systems, where removal of unwanted components is totally accomplished by scrubbing with a strongly regenerated solvent.

In regenerating the scrubbing solvents, the aspect of lowering the pressure and heating the solvents is possible to remove from the solvent the scrubbed solutes in accordance with their solubilities in the solvent.

The process and apparatus of the invention will now be described in greater detail with reference to FIG. 1.

In this particular embodiment, acid gases and $C_3$ and heavier hydrocarbons are to be separated from a petroleum gas. The treated gas is to be released at a pressure of approximately 60.5 bars. As previously explained, should this release pressure be substantially lower, complete $C_3$ and heavier hydrocarbon separation could have been carried out by fractionation and the acid gases removed by scrubbing before or after the fractionation. However, with this high pressure release, fractionation cannot be carried out with specificity in view of the critical pressure of the resulting mixtures, so that the remainder $C_3$ hydrocarbon separation is accomplished during the scrubbing stage. Therefore, during the fractionation of the gaseous mixture, approximately 50% of the $C_3$ hydrocarbons pass out of the fractionation column overhead and the remainder is drawn off in the column bottom. To maintain a pressure in the column bottom, which is lower than the critical, appropriate amounts of methane and ethane have to remain in the bottoms.

Fed through line 1, at approximately 40,000 kmol/hr is a gas at a temperature of 316 K and a pressure of 63 bars. The gas has the following composition:

| | |
|---|---|
| $CH_4$ | 73.71 Mol-% |
| $C_2H_6$ | 9.53 Mol-% |
| $C_3H_8$ | 6.08 Mol-% |
| $C_4$-hydrocarbons | 3.03 Mol-% |
| $C_{5+}$-hydrocarbons | 1.18 Mol-% |
| $N_2$ | 0.13 Mol-% |
| $CO_2$ | 6.34 Mol-% |
| $H_2S$ | 25 ppm. |

The gas is first cooled in heat exchanger 2 by exchange with the treated product gas flowing in lines 12 and 19. The entry gas is cooled in exchanger 2 to approximately 296 K prior to entering separator 3. The liquid, which is rich in the higher hydrocarbons, is removed from separator 3 via line 4. The gases leave separator 3 vis line 5 where the gases are split and passed to heat exchangers 6 and 7, where the gases are further cooled prior to joined entry into fractionation column 8. The temperature of the gases prior to entry is approximately 265 K.

The fractionation column 8 has head cooling and sump heating, where the heat temperature is at approximately 244 K and the sump temperature is at approximately 319 K. The operating pressure for the fractionating column is at approximately 61.6 bar. The critical pressure for this particular gas composition of the rectified liquid is above 70 bars at all points in the column which is sufficiently far away from the operating pressure. The critical pressures of the individual hydrocarbons are all below the operating pressure, examples of which are as follows: Methane 46.2 bars; ethane 48.8 bars; and propane 42.5 bars.

The overhead product of the column, leaving via line 9, has the following composition:

| | |
|---|---|
| $CH_4$ | 81.23 Mol-% |
| $C_2H_6$ | 8.40 Mol-% |
| $C_3H_8$ | 3.26 Mol-% |
| $C_4$-hydrocarbons | 0.54 Mol-% |
| $C_{5+}$-hydrocarbons | 0.00 Mol-% |
| $N_2$ | 0.15 Mol-% |
| $CO_2$ | 6.42 Mol-% |
| $H_2S$ | 21 ppm. |

The bottoms product of the fractionation column is removed via line 10 and has the following composition:

| | |
|---|---|
| $CH_4$ | 20.07 Mol-% |
| $C_2H_6$ | 18.50 Mol-% |
| $C_3H_8$ | 27.43 Mol-% |
| $C_4$-hydrocarbons | 20.97 Mol-% |
| $C_{5+}$-hydrocarbons | 6.97 Mol-% |
| $CO_2$ | 6.06 Mol-% |
| $H_2S$ | 55 ppm. |

From the above composition of the overhead and bottom products, it is apparent that a substantial portion of the methane is removed with the overhead, whereas major portion of the higher hydrocarbons $C_3$, $C_4$ and $C_5$ are removed with the bottoms. In this particular aspect, none of the $C_{5+}$-hydrocarbons are removed with the overhead. Further there is a split in the amount of carbon dioxide and hydrogen sulphide removed with the overhead and bottoms. The overhead product is now ready for the scrubbing stage. The overhead passes through line 9 and is heated slightly in exchanger 7 as it exchanges with the entering gases from separator 3. The overhead passes to the lower end of a first scrubbing column 11 which is equipped with intermediate cooling. The solvent, in this instance methanol, is sprayed downwardly of the column at a temperature of approximately 238 K at a rate of approximately 2,000 tons per hour. The solvent scrubs from the upwardly travelling gases the higher hydrocarbons, hydrogen sulphide and carbon dioxide. The product leaving the scrubbing tower is at a temperature of approximately 238 K. The composition is heated in exchanger 6 to 273 K and then further heated in exchanger 2 where it releases its remaining cold content. The product gas flowing in line 13, which is now ready for a long distance transport, consists of 92.51 Mol-% methane; 7.32 Mol-% ethane and 0.17 Mol-% nitrogen. Therefore, the cleansed or treated gas is free of the unwanted impurities of the higher $C_3$ through $C_5$ hydrocarbons, the carbon dioxide and hydrogen sulphide gases.

The spent solvent is removed from the base of the scrubbing column 11, relieved to pressure of 21 bars in pressure-reducing valve 14 and then passes into separator 15. The composition of the gas from separator 15 is as follows: 72.50 Mol-% methane; 14.64 Mol-% ethane; 9.82 Mol-% carbon dioxide and remainder heavy hydrocarbons. This gas, together with a gas brought in from line 33, passes to compressor 16 which returns it to the operating pressure of the scrubbing column 11 for purposes of recycle.

The liquid from separator 15 is relieved in pressure-relief valve 17 to a pressure of approximately 2 bars and is fed to the second scrubbing column 18. The column has methanol sprayed downwardly therein. The temperature at the top of this column is approximately 243 K, while some heating is applied to the sump of the column.

The gases released by the second scrubbing column 18 are transferred via line 19 to release their cold content in heat exchangers 6 and 2. The gases exiting line 20 have the following composition:

22.2 Mol-% methane; 27.23 Mol-% ethane; 6.94 Mol-% propane and 43.63 Mol-% carbon dioxide. No hydrogen sulphide is present in this gas, therefore, it may be used for purposes of heating or the like.

The sump liquid from the second scrubbing column is raised by pump 21 to pressure of approximately 4 bars and passes, after heating in heat exchanger 22, to the upper part of regeneration fractionation column 23. The head temperature of the fractionation column is maintained at approximately 298 K and the sump temperature at 381 K. In column 23 almost all of the unwanted constituents in the liquid are removed in the overhead product. The sump liquid(practically pure methanol) of tower 23 is brought up to pressure before transfer to column 11 by pump 24, while the temperature thereof is brought up to that of column 11 by heat exchangers 22 and 35. The quantity of solvent required for column 18 is removed from line 25 before heat exchanger 35 and the pressure reduced by valve 26.

The gases from the overhead of the regeneration column 23 which are free of $C_1$, $C_2$ hydrocarbons and consist mainly of $C_3$ hydrocarbons, carbon dioxide and hydrogen sulphide, is compressed in compressor 27 to approximately 24 bars. The gas is precooled in cooler 28 and is cooled further in the sump of second scrubbing column 18 and then passed through line 29 to rectification column 30, having head cooling and sump heating. The head temperature is maintained at approximately 240 K. Added to column 30 through line 4 are the liquid portions from separator 3 which have been relieved in pressure-relief valve 31 and the liquid from fractionation column 8, which passes through line 10 and is relieved in pressure-relief valve 32. Column 30 fractionates the mixture of gases into a head fraction of 41.56 Mol-% methane; 34.34 Mol-% ethane; 0.59 Mol-% propane; 23.51 Mol-% carbon dioxide and 20 ppm of hydrogen sulphide. This head product passes through line 33 to above gas separator 15 which is then joined with the gases emerging from separator 15. As explained, these gases are compressed in compressor 16 prior to entry to scrubbing column 11. The bottoms of the fractionation column 30 are made up of 54.62 Mol-% propane; 32.62 Mol-% $C_4$ hydrocarbons; 12.70 Mol-% $C_{5+}$-hydrocarbons; 0.03 Mol-% carbon dioxide and 0.03 Mol-% hydrogen sulphide. The bottoms are passed to a conditioning unit 34 shown diagramatically. This mixture of hydrocarbons may be further fractionated or treated as required by known methods to obtain the desired fractions.

From the detailed description of the preferred embodiments, it is apparent that a gas under high pressure may be treated by this process to yield a gas free of the unwanted components at the same high pressure without the need for any intermediate pressure relief of the gases and subsequent recompression.

The regeneration of solvent takes place in a fractionation column 23, whereby recovery of the methanol from the bottoms is achieved along with substantially complete removal of the un-wanted gases in the overhead, so that principally the $C_3$ constituents, carbon dioxide and hydrogen sulphide, are transferred to the fractionation column 30 to complete the removal of the hydrogen sulphide along with the higher hydrocarbons and carbon dioxide.

Although various embodiments of the invention have been described herein in detail, it will be understood by those skilled in the art that variations may be made thereto without departing from the spirit of the invention or scope of the appended claims.

The embodiments of the invention in which an exclusive property or privilege is claimed are defined as follows:

1. A process for treating an incoming gaseous mixture under pressure which includes methane, ethane, hydrogen, nitrogen and unwanted components of $C_3$, $C_4$ and $C_5$ higher hydrocarbons, hydrogen sulphide and carbon dioxide, said process comprising fractionating at a pressure between the critical pressures of the individual hydrocarbon constituents and the lowest critical pressure of the liquid mixtures formed during fractionation such gaseous mixture to remove at least minor portions of higher hydrocarbons, hydrogen sulphide and carbon dioxide in a bottom product, scrubbing overhead product from said fractionation step to remove in a suitable solvent a substantial remainder of $C_3$, $C_4$ and $C_5$ higher hydrocarbons, hydrogen sulphide and carbon dioxide from said overhead product to give a gaseous mixture essentially free of said unwanted components.

2. A process of claim 1, wherein scrubbing of the gases is carried out at a temperature below 0° C.

3. A process of claim 1, wherein the scrubbing is carried out at a temperature approximate the temperature of the top of the fractionation column.

4. A process of claim 1, wherein the scrubbing is carried out at a pressure approximate the pressure of the fractionation column.

5. A process of claim 1, wherein the scrubbing solvent is fed to a regeneration fractionation column wherein unwanted components of propane, hydrogen sulphide and carbon dioxide are separated from the scrubbing solvent, such gases from the second fractionation column are fed to a third fractionation column into which liquid products from the first fractionation column are also fed, said third fractionation column separating principally the $C_3$, $C_4$ and $C_5$ hydrocarbons, carbon dioxide and hydrogen sulphide from the mixtures, the gases from the third fractionation column being re-cycled into the scrubbing stage.

6. A process of claim 1, wherein the liquid phases forming during the rectification and during a preceding condensation are released to a lower pressure and subjected to a further rectification in which the inert gases, light hydrocarbons and eventually carbondioxide are expelled, recompressed and fed into the scrubbing.

7. A process of claim 1, wherein $C_{5+}$-hydrocarbons are totally removed with the bottoms product.

8. A process of claim 1, wherein $C_{4+}$-hydrocarbons are removed with the bottoms product.

9. A process of claim 1, wherein $C_{3+}$-hydrocarbons and hydrogen sulphide are principally removed with the bottoms product.

10. A process of claim 1, wherein such gaseous mixture is partially liquified and separated prior to fractionation of resultant cooled gases.

11. A process of claim 10, wherein a major portion of the higher hydrocarbons are removed with the formed liquid as separated from the partially liquified gaseous mixture.

12. A process of claim 1, wherein a polar organic solvent is used in the scrubbing stages.

13. A process of claim 12, wherein the scrubbing solvent is methanol.

* * * * *